United States Patent [19]

Hellqvist

[11] Patent Number: 4,481,818

[45] Date of Patent: Nov. 13, 1984

[54] METHOD OF DETECTING CRACKS IN CONSTRUCTIONS

[75] Inventor: Kjell A. Hellqvist, Genarp, Sweden

[73] Assignee: Kockums AB, Malmo, Sweden

[21] Appl. No.: 375,126

[22] PCT Filed: Aug. 18, 1981

[86] PCT No.: PCT/SE81/00230

§ 371 Date: Apr. 19, 1982

§ 102(e) Date: Apr. 19, 1982

[87] PCT Pub. No.: WO82/00718

PCT Pub. Date: Mar. 4, 1982

[30] Foreign Application Priority Data

Aug. 26, 1980 [SE] Sweden ............................ 8005963

[51] Int. Cl.³ .................................................. G01N 29/04
[52] U.S. Cl. .......................................................... 73/587
[58] Field of Search ................, 73/587, 658, 659, 801; 367/127, 129

[56] References Cited

U.S. PATENT DOCUMENTS

| 3,286,224 | 11/1966 | Zefting | 367/125 |
| 3,924,456 | 12/1975 | Vahaviolos | 73/587 |
| 3,985,024 | 10/1976 | Horak | 73/587 |
| 4,009,463 | 2/1977 | Vercellotti et al. | 73/587 |
| 4,033,179 | 7/1977 | Romrell | 73/587 |
| 4,128,011 | 12/1978 | Savage | 73/632 |
| 4,269,065 | 5/1981 | Clark | 73/660 |
| 4,317,186 | 2/1982 | Nishi et al. | 367/127 |
| 4,380,172 | 4/1983 | Imam et al. | 73/587 |

Primary Examiner—Stephen A. Kreitman
Assistant Examiner—John E. Chapman, Jr.

[57] ABSTRACT

A process for monitoring the presence of cracks, formation of cracks and growth of cracks in constructions, for example off-shore oil and gas platforms, by recording and analysis of acoustic emissions from the construction, the sensors being mounted in the medium which surrounds the construction instead of on or in the construction itself.

5 Claims, 2 Drawing Figures

METHOD OF DETECTING CRACKS IN CONSTRUCTIONS

The present invention relates to a method of detecting preferably continuously, the presence of cracks, the formation of cracks and the growth of cracks in constructions by recording and analysis of acoustic emission from a crack in the construction.

The need for a continuous monitoring of crack formation and crack growth is particularly obvious in the case of complex steel constructions with construction elements which are difficult of access for visual inspection and testing by conventional testing methods. One example of this is off-shore platforms which are exposed for a long time to heavy loading and fatigue stresses while at the same time the platforms are in a corrosive medium, which increases the risk of crack formation. Large cracks can lead to breakage and in the worse case to wrecking with serious damage as a consequence. Because of this, the requirements of authorities and classification societies are comprehensive when it is a question of preventive checking and measures to avoid wrecking. The annual checks of underwater constructions in the North Sea for example comprise primarily cleaning and visual inspection. Crack checks and repairs are carried out as necessary. Every five years, larger checks are carried out but for reasons of cost they are limited to parts of the platform where the risks of corrosion and crack formation are regarded as being greatest, that is to say, to about 10% of the platform construction. A continuous monitoring of crack formation and crack growth which covers the whole platform would naturally be desirable so as to prevent wrecking caused by crack formation in a more reliable manner than has hitherto been the case. As a result of the wrecking of platforms which has occurred in recent times, it may be expected that the regulations regarding preventive checking may be sharpened.

A known crack detecting system which renders possible continuous detection of crack formation and crack growth utilizes the known phenomenon that crack formation and crack growth gives rise to acoustic emission in the construction material. By fitting a plurality of sensors, which are sensitive to the acoustic emission caused by the crack, on the surface of the construction element and recording and analyzing the signals which the sensors deliver depending on acoustic emission, as well as the differences in time between the recordings of the various sensors, an accurate detection of the position and growth of even very small cracks in the construction element has been rendered possible.

A disadvantage of said known crack detecting system is that the sensors must be fitted to the surface of the construction element which is to be tested, so that it is necessary to determine in advance which parts of the construction shall form the subject of crack detecting. Also, when this known method is applied to constructions with a complex formation, for example off-shore platforms, it has therefore been necessary to select in advance a limited number of observation points which are judged to be particularly exposed from the crack point of view. It would actually be far too expensive and difficult to carry out in practice to utilize the said known method to provide an overall crack detection on all the load-bearing construction elements included in the platform.

The object of the present invention is to provide a method of detecting cracks which is admittedly based on recording and analysis of acoustic emission from a crack but which does not suffer from the disadvantages mentioned above and which thus renders possible a continuous and comprehensive crack detection even in complex constructions, using only a few sensors.

The method according to the invention detects the presence of cracks, the formation of cracks and the growth of cracks in constructions by recording and analysis of acoustic emissions from a crack in the construction using at least two sensors sensitive to the acoustic vibrations emitted from the crack to the medium adjacent to the construction. The sensors are mounted in the medium, spaced apart in accurately defined positions in relation to the construction; measure the differences in time between the recordings by the various sensors of the acoustic vibrations emitted from a crack in the construction to said medium; and from these time differences the location of the crack is determined.

The invention is described in more detail with reference as an example to the embodiment illustrated in the accompanying Figures.

Figure 1:
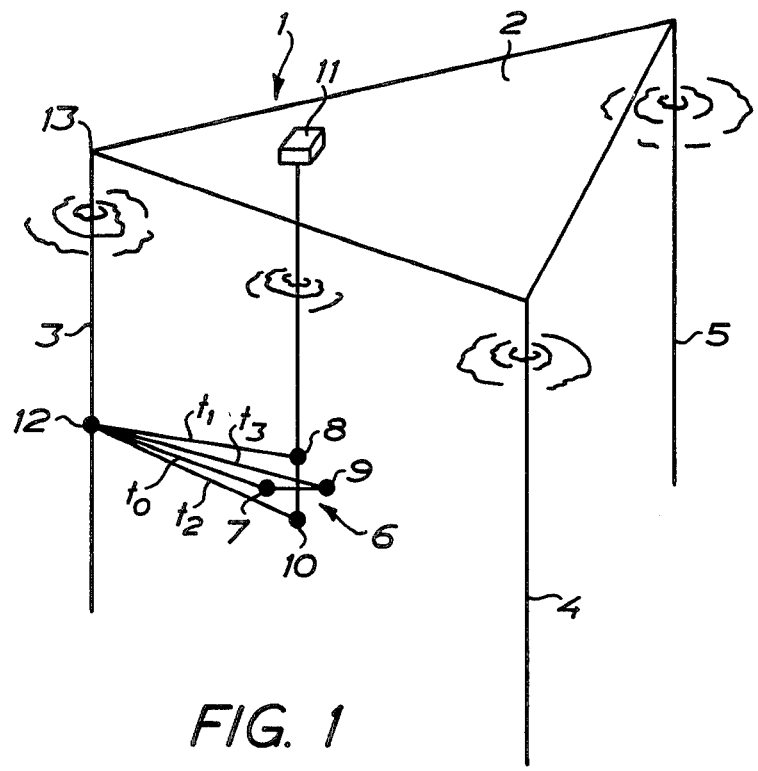
FIG. 1 illustrates the application of the invention to an off-shore platform shown diagrammatically and in the leg of which a crack is indicated.

The invention is based on the knowledge that crack formation and crack growth give rise to acoustic emission not only in the construction element in which the crack appears but also in the adjacent medium. If the construction element is in a gaseous medium, for example air, acoustic vibrations are emitted to the air surrounding the construction element and if the construction element is surrounded by liquid, for example water, as is the case with off-shore platforms, acoustic vibrations are emitted to the water surrounding the construction element. According to the invention, a plurality of sensors for measuring acoustic emission from a crack to the medium are mounted in the medium which is adjacent to or surrounds the construction. Recording and analysis of the signals from the sensors therefore renders it possible to determine the position of the emission source in relation to the sensors. If the construction element is surrounded by a gaseous medium, for example air, microphones are used as sensors. If the medium to which the construction element is adjacent is a liquid, for example water, hydrophones are used as sensors.

The sensors are placed with a mutual spacing apart in accurately defined positions in relation to the construction which is to be tested. The signals from the sensors are transmitted to a signal analysis system in a computor in which the position of the sensors in relation to the construction is programmed. The geometry of the construction is preferably also programmed in the computor so that the position of the detected crack can be presented directly in the form of distance from selected fixed points in the construction.

The method according to the invention presupposes the use of at least two sensors. A measurement of the difference in time between the recording of the two sensors of the acoustic vibrations emitted from a crack renders possible a mathematical determination of a hyperboloid of such a nature that an emission source situated at any point on said hyperboloid gives rise to the measured difference in time between the recordings of the sensors. The section where this hyperboloid intersects a construction element thus represents a section in which the crack may be present. If the hyperboloid only intersects one construction element, the crack from which the coustic emission originates must be situated in this section.

A more accurate determination of the position of the crack is obtained if the acoustic emission from three sensors is recorded. The differences in time between the recordings of the sensors then render it possible to determine a line which constitutes the secant between two hyperboloids and which is of such a nature that an emission source situated at any point on the line gives rise to the measured differences in time between the recordings of the sensors.

Thus, the emission source, that is to say the crack, can be situated where this line intersects the construction. If the line intersects the construction at only one place, the crack must be situated on this secant with the construction.

In the preferred embodiment according to the invention, however, four sensors are used. The differences in time between the recordings of the sensors of the acoustic vibrations emitted from a crack then render possible a determination of the position of the emission source at a point which constitutes the point of intersection between two lines each of which in turn constitutes the secant between two hyperboloids. The use of four sensors thus provides a precise determination of the distance and direction of the emission source, that is to say the crack, from the sensors.

In FIG. 1 an application of the invention to a submerged platform construction 1 is illustrated most diagrammatically. The platform construction comprises on the one hand a foundation 2 for equipment not shown in the figure and on the other hand three legs 3, 4 and 5, which support the foundation and which extend downwards and are surrounded by water. At an accurately determined position in relation to the platform construction a sensor unit 6 is disposed, submerged in the water and comprises four hydrophones 7, 8, 9, 10 with well defined mutual spacing apart. The acoustic characteristics of the hydrophones must be selected so that a measurement of frequencies is rendered possible within a substantial part of the frequency range for the acoustic emission from a crack. The sensor unit 6 and hence each of the hydrophones 7-10 is connected by means of signal-transmitting cables to a computor 11 on the platform foundation so that signals from the hydrophones 7-10 are fed into the computor 11 for processing and analysis of the signals.

If a crack 12 appears in the leg 3, the crack gives rise to the emission of acoustic vibrations on the one hand in the leg 3 but also in the water which surrounds the leg. The acoustic vibrations are recorded in turn by the hydrophones 7, 8, 9 and 10 with the time intervals $t_1-t_0$, $t_2-t_0$ and $t_3-t_0$. The signals from the hydrophones 7-10 are fed into the computor 11 where a signal analysis is carried out to determine the emission source, that is to say the position of the crack 12 in relation to the sensor unit 6. If the geometry of the platform construction 1 is also stored in the computor 11, a direct indication of the position of the crack 12 in relation to a selected fixed point, for example the corner 13, on the platform construction is obtained through the signal analysis.

Figure 2:
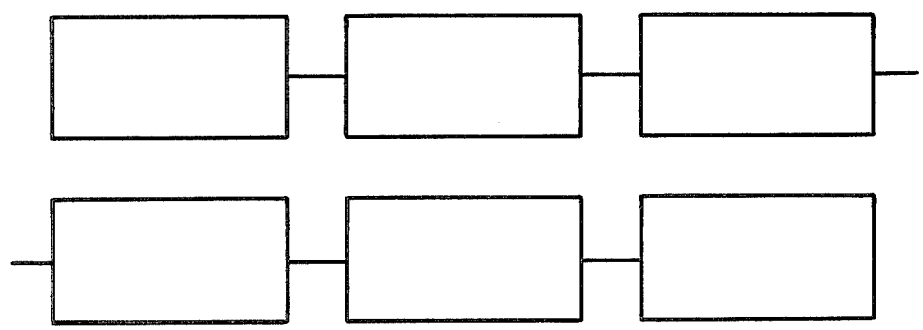
FIG. 2 shows a basic block diagram for processing of the signals obtained from the pick-offs.

The signal processing is illustrated in the block diagram shown in FIG. 2. The signals from the sensors, which may consist of microphones or hydrophones, are amplified in an amplifier and then conveyed through a filter where background noise and extraneous interference signals are filtered out. The analogue signals coming from the filter are converted into digital form in an A/D converter and are then fed into the computor for signal analysis with a signal analysis program. Programs for such signal analysis are known in principle and used in previously known crack detecting systems based on the analysis of acoustic emission. The result is shown on a recorder where the current crack situation can thus be read off continuously.

I claim:
1. A method for detecting the presence of cracks, the formation of cracks and the growth of cracks in constructions by recording and analysis of acoustic emissions from a crack in the construction, comprising:
   (1) immersing in a liquid medium adjacent to construction, in spaced apart accurately-defined positions in relation to the construction, at least two sensors sensitive to the acoustic emissions from the crack to the medium;
   (2) sensing and recording the acoustic emissions to said medium sensed by each sensor;
   (3) measuring the differences in time between the sensing and recording of such acoustic emissions by each sensor; and
   (4) determining from said differences in time the location of the crack.

2. A method as claimed in claim 1 in which at least four sensors measure the differences in time between the sensing and recording of the acoustic emissions and determine both the distance from the sensors and the orientation of the crack.

3. A method as claimed in claim 1 in which signals from the sensors are fed into a signal analysis system in a computer which is programmed to determine the location of the crack from the position of the sensors in relation to the construction.

4. A method as claimed in claim 3 in which the geometry of the construction is also programmed in the computer.

5. A method as claimed in claim 1 in which the sensors are hydrophones immersed in the liquid.

* * * * *